(12) United States Patent
Khalil et al.

(10) Patent No.: US 12,656,330 B2
(45) Date of Patent: Jun. 16, 2026

(54) SILVER NANONEEDLES FOR SUSTAINED DC CURRENT SINGLE NANOPORE MEASUREMENTS

(71) Applicant: University of Cincinnati, Cincinnati, OH (US)

(72) Inventors: Essraa Abdelwahab Hussein Khalil, Cincinnati, OH (US); Ryan White, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 891 days.

(21) Appl. No.: 17/852,315

(22) Filed: Jun. 28, 2022

(65) Prior Publication Data

US 2022/0412949 A1     Dec. 29, 2022

Related U.S. Application Data

(60) Provisional application No. 63/215,960, filed on Jun. 28, 2021.

(51) Int. Cl.
| | |
|---|---|
| *G01N 33/487* | (2006.01) |
| *G01N 33/543* | (2006.01) |
| *G01N 33/68* | (2006.01) |

(52) U.S. Cl.
CPC . *G01N 33/48721* (2013.01); *G01N 33/54373* (2013.01); *G01N 33/6896* (2013.01); *G01N 2800/2821* (2013.01)

(58) Field of Classification Search
CPC ....... G01N 33/48721; G01N 33/54373; G01N 33/6896; G01N 2800/2821
See application file for complete search history.

(56) References Cited

PUBLICATIONS

"Simple procedure for the fabrication of silver/silver chloride potentiometric electrodes with micrometre and smaller dimensions: application to scanning electrochemical microscopy", Analyst, 2000, 125, 889â893 (Year: 2000).*
"Reproducible Electrochemical Etching of Silver Probes with a Radius of Curvature of 20 nm for Tip-Enhanced Raman Applications" Applied Physics Letters 99, 143108 (2011). (Year: 2011).*
"Spatially Resolved Chemical Detection with a Nanoneedle-Probe-Supported Biological Nanopore" ACS Nano 2019 13 (2), 2606-2614. (Year: 2019).*
Bayley, H. & Martin, C. R. Resistive-pulse sensing—from microbes to molecules. Chem. Rev. 100, 2575-2594 (2000).

(Continued)

*Primary Examiner* — Dennis White
(74) *Attorney, Agent, or Firm* — Brent M. Peebles

(57) ABSTRACT

A composition having one or more nanoneedles is provided, where each nanoneedle has a silver tip and one or more of the silver tips comprise an AgCl layer. In one approach, one or more of the silver tips further include a layer of thiol-polyethylene glycol. A method of resistive pulse detection involving a protein pore is also provided. The method involves reconstituting one or more protein pores in a lipid membrane formed on the tip of a nanoneedle, then applying a potential across the membrane and detecting resistive pulses.

12 Claims, 17 Drawing Sheets

(56)     References Cited

PUBLICATIONS

Kozak, D., Anderson, W., Vogel, R. & Trau, M. Advances in resistive pulse sensors: Devices bridging the void between molecular and microscopic detection. Nano Today 6, 531-545 (2011).

Pan, R., Hu, K., Jiang, D., Samuni, U. & Mirkin, M. V. Electrochemical Resistive-Pulse Sensing. J. Am. Chem. Soc. 141, 19555-19559 (2020).

Wanunu, M., Morrison, W., Rabin, Y., Grosberg, A. Y. & Meller, A. Electrostatic focusing of unlabelled DNA into nanoscale pores using a salt gradient. Nat. Nanotechnol. 5, 160-165 (2010).

Shoji, K., Kawano, R. & White, R. J. Recessed Ag/AgCl Microelectrode-Supported Lipid Bilayer for Nanopore Sensing. Anal. Chem. 92, 10856-10862 (2020).

Wang, Y., Zheng, D., Tan, Q., Wang, M. X. & Gu, L. Q. Nanopore-based detection of circulating microRNAs in lung cancer patients. Nat. Nanotechnol. 6, 668-674 (2011).

Zhang, X., Wang, Y., Fricke, B. L. & Gu, L. Q. Programming nanopore ion flow for encoded multiplex microRNA detection. ACS Nano 8, 3444-3450 (2014).

Akeson, M., Branton, D., Kasianowicz, J. J., Brandin, E. & Deamer, D. W. Microsecond time-scale discrimination among polycytidylic acid, polyadenylic acid, and polyuridylic acid as homopolymers or as segments within single RNA molecules. Biophys. J. 77, 3227-3233 (1999).

Boersma, A. J., Brain, K. L. & Bayley, H. Real-time stochastic detection of multiple neurotransmitters with a protein nanopore. ACS Nano 6, 5304-5308 (2012).

Macazo, F. C. & White, R. J. Monitoring charge flux to quantify unusual ligand-induced ion channel activity for use in biological nanopore-based sensors. Anal. Chem. 86, 5519-5525 (2014).

Boersma, A. J. & Bayley, H. Continuous Stochastic Detection of Amino Acid Enantiomers with a Protein Nanopore. Angew. Chemie 124, 9744-9747 (2012).

Piguet, F. et al. Identification of single amino acid differences in uniformly charged homopolymeric peptides with aerolysin nanopore. Nat. Commun. 9, (2018).

Kowalczyk, S. W., Hall, A. R. & Dekker, C. Detection of local protein structures along DNA using solid-state nanopores. Nano Lett. 10, 324-328 (2010).

Watanabe, H. et al. Analysis of Pore Formation and Protein Translocation Using Large Biological Nanopores. Anal. Chem. 89, 11269-11277 (2017).

Clarke, J. et al. Continuous base identification for single-molecule nanopore DNA sequencing. Nat. Nanotechnol. 4, 265-270 (2009).

Venkatesan, B. M. & Bashir, R. Nanopore sensors for nucleic acid analysis. Nat. Nanotechnol. 6, 615-624 (2011).

Varongchayakul, N., Song, J., Meller, A. & Grinstaff, M. W. Single-molecule protein sensing in a nanopore: a tutorial. Chem. Soc. Rev. 47, 8512-8524 (2018).

Adam R. Hall, Andrew Scott, Dvir Rotem, Kunal K. Mehta, Hagan Bayley, and C. D. Hybrid pore formation by directed insertion of alpha hemolysin into solid-state nanopores. Bone 23, 1-7 (2012).

Shi, W., Friedman, A. K. & Baker, L. A. Nanopore Sensing. Anal. Chem. 89, 157-188 (2017).

Song, Y., Zhang, J. & Li, D. Microfluidic and nanofluidic resistive pulse sensing: A review. Micromachines 8, 1-19 (2017).

Macazo, F. C. & White, R. J. Bioinspired Protein Channel-Based Scanning Ion Conductance Microscopy (Bio-SICM) for Simultaneous Conductance and Specific Molecular Imaging. J. Am. Chem. Soc. 138, 2793-2801 (2016).

Lazenby, R. A., Macazo, F. C., Wormsbecher, R. F. & White, R. J. Quantitative Framework for Stochastic Nanopore Sensors Using Multiple Channels. Anal. Chem. 90, 903-911 (2018).

Mueller, P., Rudin, D. O., Ti Tien, H. & Wescott, W. C. Reconstitution of Cell Membrane Structure in vitro and its Transformation into an Excitable System. Nature 194, 979-980 (1962).

Derrington, I. M. et al. Nanopore DNA sequencing with MspA. Proc. Natl. Acad. Sci. U. S. A. 107, 16060-16065 (2010).

Montal, M. & Mueller, P. Formation of bimolecular membranes from lipid monolayers and a study of their electrical properties. Proc. Natl. Acad. Sci. U. S. A. 69, 3561-3566 (1972).

M. Sugawara, A. H. Advances in Planar Lipid Bilayers and Liposomes. (Elsevier Amsterdam, The Netherlands, 2005).

Hirano-Iwata, A., Niwano, M. & Sugawara, M. The design of molecular sensing interfaces with lipid-bilayer assemblies. TrAC—Trends Anal. Chem. 27, 512-520 (2008).

Kawano, R. et al. Automated parallel recordings of topologically identified single ion channels. Sci. Rep. 3, 1-7 (2013).

Funakoshi, K., Suzuki, H. & Takeuchi, S. Lipid bilayer formation by contacting monolayers in a microfluidic device for membrane protein analysis. Anal. Chem. 78, 8169-8174 (2006).

Shoji, K. & Kawano, R. Microfluidic formation of double-stacked planar bilayer lipid membranes by controlling the water-oil interface. Micromachines 9, (2018).

Bayley, H. et al. Droplet interface bilayers. Mol. BioSyst. 4, 1191-1208 (2008).

Hwang, W. L., Holden, M. A., White, S. & Bayley, H. Electrical behavior of droplet interface bilayer networks: Experimental analysis and modeling. J. Am. Chem. Soc. 129, 11854-11864 (2007).

Yanagisawa, M., Iwamoto, M., Kato, A., Yoshikawa, K. & Oiki, S. Oriented reconstitution of a membrane protein in a giant unilamellar vesicle: Experimental verification with the potassium channel KcsA. J. Am. Chem. Soc. 133, 11774-11779 (2011).

White, R. J. et al. Single ion-channel recordings using glass nanopore membranes. J. Am. Chem. Soc. 129, 11766-11775 (2007).

A. Ottova, H. T. T. Advances in Planar Lipid Bilayers and Liposomes. (Elsevier, 2005).

Zhou, Y., Bright, L. K., Shi, W., Aspinwall, C. A. & Baker, L. A. Ion channel probes for scanning ion conductance microscopy. Langmuir 30, 15351-15355 (2014).

Shi, W. et al. Membrane patches as ion channel probes for scanning ion conductance microscopy. Faraday Discuss. 193, 81-97 (2016).

Shi, W. et al. Characterization of Membrane Patch-Ion Channel Probes for Scanning Ion Conductance Microscopy. Small 14, 1-10 (2018).

Richter, R. P., Berat, R. & Brisson, A. R. Formation of solid-supported lipid bilayers: An integrated view. Langmuir 22, 3497-3505 (2006).

Tien, H. T. & Ottova, A. L. Supported planar lipid bilayers (s-BLMs) as electrochemical biosensors. Electrochim. Acta 43, 3587-3610 (1998).

Naumann, R. et al. Incorporation of Membrane Proteins in Solid-Supported Lipid Layers. Angew. Chemie Int. Ed. English 34, 2056-2058 (1995).

Okuno, D. et al. A simple method for ion channel recordings using fine gold electrode. Anal. Sci. 32, 1353-1357 (2016).

Okuno, D. et al. A gold nano-electrode for single ion channel recordings. Nanoscale 10, 4036-4040 (2018).

Shoji, K., Kawano, R. & White, R. J. Spatially Resolved Chemical Detection with a Nanoneedle-Probe-Supported Biological Nanopore. ACS Nano (2019) doi: 10.1021/acsnano.8b09667.

Shoji, K., Kawano, R. & White, R. J. Analysis of Membrane Protein Deinsertion-Associated Currents with Nanoneedle-Supported Bilayers to Discover Pore Formation Mechanisms. Langmuir 36, 10012-10021 (2020).

Zhang, C. et al. Fabrication of silver tips for scanning tunneling microscope induced luminescence. Rev. Sci. Instrum. 82, 1-5 (2011).

Iwami, M., Uehara, Y. & Ushioda, S. Preparation of silver tips for scanning tunneling microscopy imaging. Rev. Sci. Instrum. 69, 4010-4011 (1998).

Pargar, F., Koleva, D. A., Copuroglu, O., Koenders, E. A. B. & Van Breugel, K. Evaluation of Ag/AgCl sensors for in-situ monitoring of freee chloride concentration in reinforced concrete structures. Young Res. Forum II Constr. Mater. 153-158 (2014).

Ziolkowski et al. Development of silicon-based electrochemical transducers. Anal. Methods 5, 5464-5470 (2013).

Brewer, P. J. & Brown, R. J. C. Effect of silver annealing conditions on the performance of electrolytic silver/silver chloride electrodes used in harned cell measurements of pH. Sensors 10, 2202-2216 (2010).

(56) References Cited

PUBLICATIONS

Safari, S., Selvaganapathy, P. R., Derardja, A. & Deen, M. J. Electrochemical growth of high-aspect ratio nanostructured silver chloride on silver and its application to miniaturized reference electrodes. Nanotechnology 22, (2011).

Kim, S. et al. Facial Fabrication and Characterization of Novel Ag/AgCl Chloride Ion Sensor Based on Gel-Type Electrolyte. Front. Chem. 8, 1-13 (2020).

Gray, N. J. & Unwin, P. R. Simple procedure for the fabrication of silver/silver chloride potentiometric electrodes with micrometre and smaller dimensions: Application to scanning electrochemical microscopy. Analyst 125, 889-893 (2000).

Pargar, F., Kolev, H., Koleva, D. A. & Van Breugel, K. Potentiometric Response of Ag/AgCl Chloride Sensors in Model Alkaline Medium. Adv. Mater. Sci. Eng. 2018, (2018).

Elsener, B., Zimmermann, L. & Bohni, H. Non destructive determination of the free chloride content in cement based materials. Mater. Corros. 54, 440-446 (2003).

Montemor, M. F. et al. Multiprobe chloride sensor for in situ monitoring of reinforced concrete structures. Cem. Concr. Compos. 28, 233-236 (2006).

Matsuura, H., Sato, Y., Sawaguchi, T. & Mizutani, F. Highly sensitive determination of acetylcholinesterase activity based on the chemisorption/reductive desorption-process of thiol compound on a silver electrode. Chem. Lett. 1, 618-619 (2002).

Esplandiu, M. J. & Hagenstrom, H. Functionalized self-assembled monolayers and their influence on silver electrodeposition. Solid State Ionics 150, 39-52 (2002).

Mohtat, N., Byloos, M., Soucy, M., Morin, S. & Morin, M. Electrochemical evidence of the adsorption of alkanethiols on two sites on Ag(111). J. Electroanal. Chem. 484, 120-130 (2000).

Hatchett, D. W., Stevenson, K. J., Lacy, W. B., Harris J. M. & White, H. S. Electrochemical oxidative adsorption of ethanethiolate on Ag(111). J. Am. Chem. Soc. 119, 6596-6606 (1997).

Hatchett, D. W., Uibel, R. H., Stevenson, K. J., Harris, J. M. & White, H. S. Electrochemical measurement of the free energy of adsorption of n-alkanethiolates at Ag(111). J. Am. Chem. Soc. 120, 1062-1069 (1998).

Moellerfeld, J., Prass, W., Ringsdorf, H., Hamazaki, H. & Sunamoto, J. Improved stability of black lipid membranes by coating with polysaccharide derivatives bearing hydrophobic anchor groups. BBA—Biomembr. 857, 265-270 (1986).

Gross, L. C. M., Heron, A. J., Baca, S. C. & Wallace, M. I. Determining membrane capacitance by dynamic control of droplet interface bilayer area. Langmuir 27, 14335-14342 (2011).

Wang, J., Benier, L. & Winterhalter, M. Quantifying Permeation of Small Charged Molecules across Channels: Electrophysiology in Small vols. ACS Omega 3, 17481-17486 (2018).

Gu, L. Q. & Bayley, H. Interaction of the noncovalent molecular adapter, B-cyclodextrin, with the staphylococcal a-hemolysin pore. Biophys. J. 79, 1967-1975 (2000).

* cited by examiner

SILVER NANONEEDLES FOR SUSTAINED DC CURRENT SINGLE NANOPORE MEASUREMENTS

CROSS REFERENCE TO RELATED APPLICATIONS

This application claims priority to U.S. Provisional Application Ser. No. 63/215,960, filed Jun. 28, 2021, which application is hereby incorporated by reference in its entirety.

STATEMENT REGARDING FEDERALLY SPONSORED RESEARCH OR DEVELOPMENT

This invention was made with government support under CHE 1608679 awarded by the National Science Foundation. The U.S. Government has certain rights in the invention.

TECHNICAL FIELD

The present invention relates to silver nanoneedle-based probes.

BACKGROUND OF THE INVENTION

Resistive pulse sensing is a sensing technique that relies on the measurement of the transient blocking current caused by single molecules entering or passing through a micro- or nanoscale orifice or pore. Nanopore-based techniques, using a biological or solid-state nanopore, have been widely applied in the detection of biomolecules such as DNA, mRNA, neurotransmitters, peptides, and proteins, in addition to the functionality of these techniques for DNA sequencing. Nanopore, resistive-pulse techniques provide single particle-to-particle readout capabilities, high sensitivity, temporal resolution, signal-to-noise, and molecular selectivity. Biological nanopores, or ion channel proteins, have attracted more interest in nanopore sensing and molecular flux imaging applications due to the atomic-level precision of the pore size. To perform resistive pulse detection with a biological nanopore, typically the protein pore is reconstituted in a lipid membrane suspended between two electrolyte compartments when a potential is applied across the membrane. When a specific analyte binds to or diffuses through the protein pore, it affects the pore conductance by physically blocking the ion channel inducing a transient blockage in the ionic current (resistive pulse). The nature of these transient blockages (e.g., magnitude, duration, and frequency) lead to molecular level discrimination, where the blockage magnitude and duration can elucidate the molecule identity, and frequency of the binding events correlates to the analyte concentration.

Biological nanopore-based techniques necessitate a stable lipid bilayer to apply ion channels as a sensing element. The formation of an artificial lipid membrane can be achieved by conventional methods such as the painting method and folding method, by using microfabricated devices, or by droplet-based techniques such as droplet-contact method, droplet interface bilayer, and droplet transfer method. Although these methods were successfully applied to form lipid bilayers, some techniques require specific tools or fabrication of microdevices such as droplet-based methods. In addition, the conventional methods are limited to the fragility of unsupported bilayers in conventional methods. On the other hand, the tip-dip method, where the lipid membrane is formed at the glass probe end, is considered a facile method to form a stable bilayer without complicated devices or tools. Moreover, this method allows for the integration of biological nanopores at the probe tip, which can be exploited not only in nanopore sensing applications but also for chemical imaging purposes such as scanning ion conductance microscopy (SICM).

The use of biological nanopores incorporated into SICM promises to bring the promising attributes of nanopore sensing to the spatial resolution and chemical imaging functionality of SICM. To achieve this, glass micro-pipets are typically employed to support the lipid bilayer for SICM measurements. Previous studies reported the use of glass pipet-supported ion channels either as a single barrel or dual barrel probe to monitor the molecular or ion flux from a porous substrate. However, the spatial resolution of the glass pipet-supported ion channels is still limited by their micrometer scale probe size.

An alternative approach to the spanning lipid bilayer method is the use of electrode supported bilayers, which have been developed and employed for sensing purposes based on ion channels. Building off these supported bilayers, prior studies developed polyethylene glycol (PEG)-modified gold nanoelectrodes to support lipid bilayer for ion channel recordings. This type of gold nanoneedle showed great promise in sensing applications and, more recently, in the ease of unzipping and reformation of the lipid bilayer throughout the measurement time. The utility of gold nanoneedle-probe-supported protein channels was recently demonstrated in the chemical detection of $\beta$-cyclodextrin ($\beta$-CD) with high spatial resolution in addition to their analysis method of protein de-insertion current for different types of pore-forming proteins and A$\beta$42 peptide associated with Alzheimer's disease. Although the gold nanoneedle platform was applied as a nanopore sensor, it exhibits a significant channel current decay, ascribed to the double layer charging at the gold electrode surface and consequently, could limit its long-term application. Therefore, a need still exists for nanoneedles that provide more stable, sustained channel current recordings.

SUMMARY OF THE INVENTION

In one embodiment, the present invention addresses that need with a composition having one or more nanoneedles, wherein each nanoneedle has a silver tip and one or more of the silver tips comprise an AgCl layer. In another embodiment, one or more of the silver tips further include a layer of thiol-polyethylene glycol. In one embodiment, the nanoneedles are electrochemically etched silver microwire. In another embodiment, the silver microwire is electrochemically etched with a perchloric acid solution. In one embodiment, the silver microwire is electrochemically etched with a nitric acid solution. In another embodiment, one or more of the silver tips are conical in shape. In one embodiment, the one or more nanoneedles have an average diameter from about 300 nm to about 600 nm. In another embodiment, the one or more nanoneedles have an average diameter from about 425 nm.

In one embodiment, the present invention is a method of resistive pulse detection involving a protein pore. The method involves reconstituting one or more protein pores in a lipid membrane formed on the tip of a nanoneedle, wherein the nanoneedle has a silver tip and one or more of the silver tips comprise an AgCl layer. Then, a potential is applied across the membrane and resistive pulses are detected. In another embodiment, one or more of the silver tips further have a layer comprising thiol-polyethylene glycol. In one embodiment, the nanoneedles are electrochemically etched silver microwire. In another embodiment, the silver microwire is electrochemically etched with a perchloric acid solution. In one embodiment, the silver microwire is electrochemically etched with a nitric acid solution. In another embodiment, one or more of the silver tips are conical in shape. In one embodiment, the one or more nanoneedles have an average diameter from about 300 nm to about 600 nm. In another embodiment, the one or more nanoneedles have an average diameter from about 425 nm. In one embodiment, the method further uses data including the resistive pulses to identify a type of molecule. In another embodiment, the data comprises the magnitude, duration, and frequency of transient blockages.

BRIEF DESCRIPTION OF THE DRAWINGS

The foregoing summary, as well as the following detailed description of preferred embodiments of the application, will be better understood when read in conjunction with the appended drawings.

FIG. 3 is a graph showing the potentiometric response of the perchloric acid etched silver versus log [Cl—] in different solutions. The linear trend reveals a Nernstian behavior over the range from 10-1-10-5M.

FIG. 4 is a graph showing the linear sweep voltammograms for reductive desorption of thiol PEG from silver nanoneedle surface in 0.1M KOH (sweep rate: 50 mV/s).

DETAILED DESCRIPTION

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

Figure 1A:
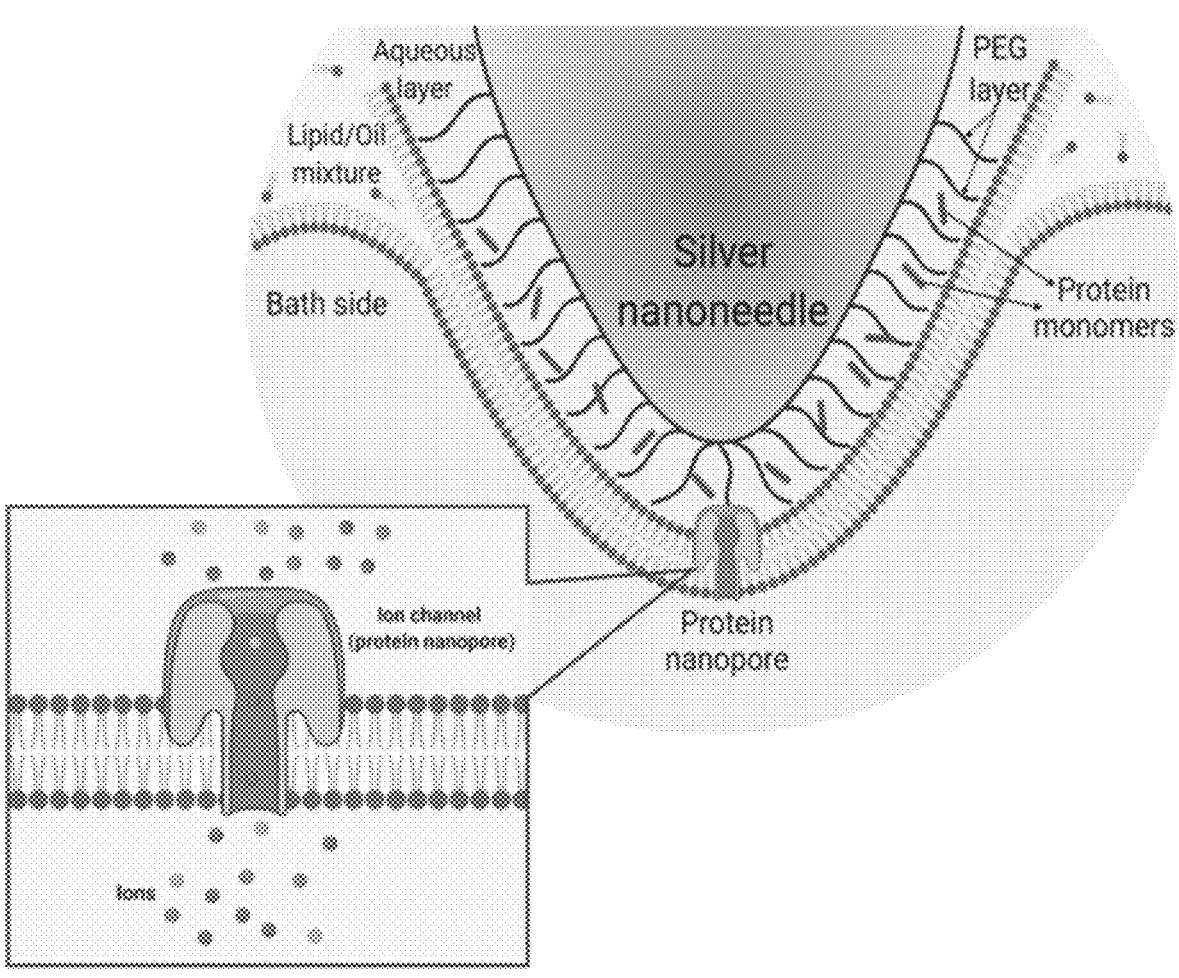
FIG. 1A is a schematic illustration of a silver nanoneedle-based ion channel probe showing alpha-hemolysin (αHL) protein insertion in the lipid membrane formed at the probe tip.
Figure 1B:
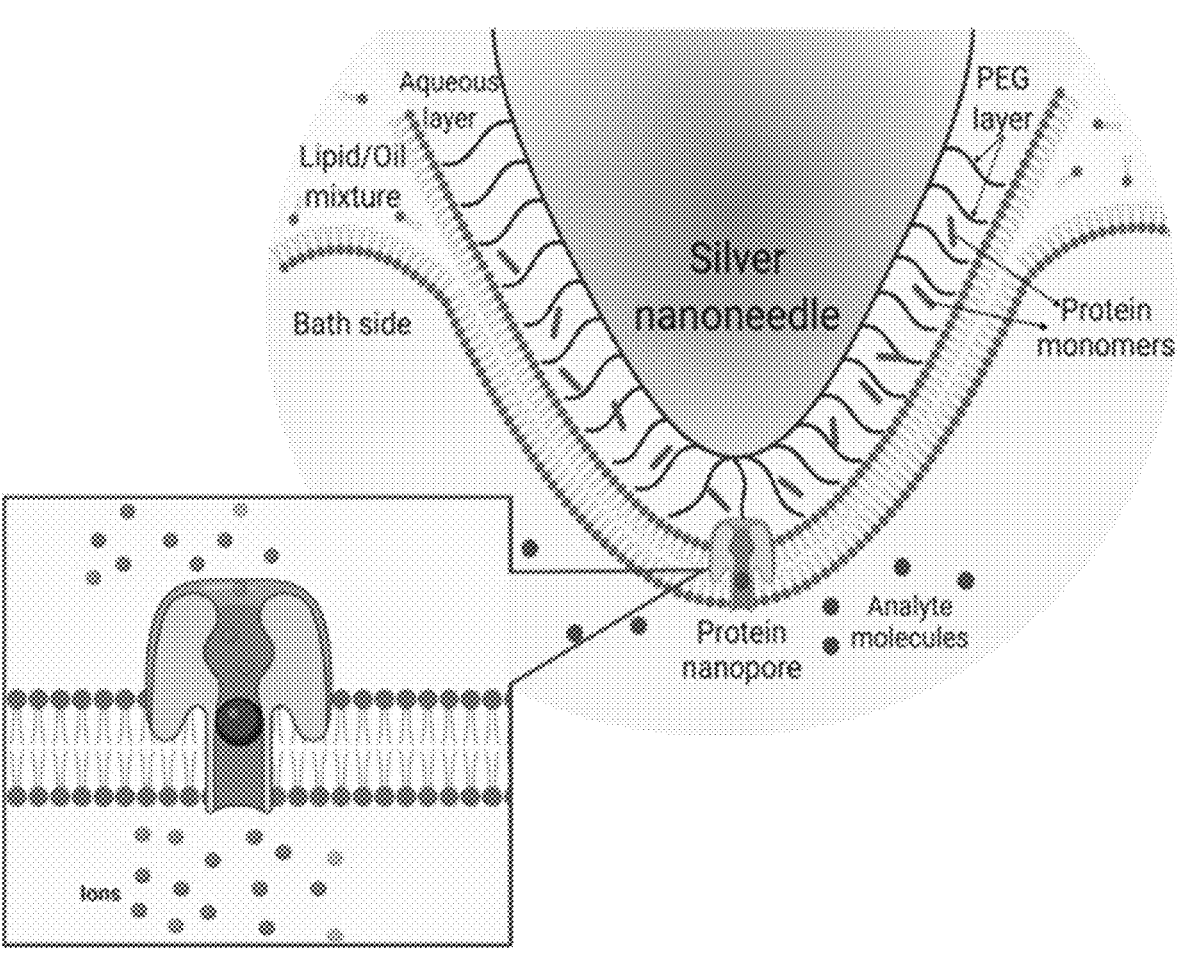
FIG. 1B is a schematic illustration of a silver nanoneedle-based ion channel probe showing S7βCD analyte molecules binding to the αHL protein pore.

The present invention involves the use of silver nanoneedle to support a lipid bilayer for ion channel measurement and single-molecule detection (FIGS. 1A and 1B). Hereinafter, "nanoneedle" means a conical or tubular needle-shaped wire in the nanometer size range (for example, a diameter or length of from about 0.1 to about 1,000 nm). In one embodiment, the nanoneedle has an average diameter from about 300 nm to about 600 nm. In another embodiment, the nanoneedle has an average diameter from about 400 nm to about 500 nm. In one embodiment, the nanoneedles of the present invention have an average diameter of about 425 nm. In one embodiment, the nanoneedle tip is conical in shape.

In one embodiment, the nanoneedles of the present invention are formed from silver. In another embodiment, the tip of the nanoneedle is silver. In one embodiment, the silver tip of the nanoneedle has a layer of silver chloride (AgCl). This AgCl layer has been confirmed by surface characterization in the examples presented below.

In one embodiment of the present invention, the surface of the silver tip of the nanoneedle is modified to create a surface layer. In another embodiment, the tip is modified with thiol-polyethylene glycol (PEG). This helps to support an artificial lipid membrane around the tip that is created when modified nanoneedle is immersed in a chamber of oil and aqueous compartments. An ion channel protein (or the protein pore) is then embedded in the formed lipid membrane to be employed for nanopore sensing.

Referring to FIG. 1A, the nanoneedle probe consists of an electrochemically-etched silver wire with thiol-PEG surface modification. The figure shows αHL protein insertion in the lipid membrane formed at the probe tip. The αHL inserts from the aqueous solution between the membrane and the silver surface. Referring to FIG. 1B, S7βCD analyte molecules in the bath side bind to the αHL protein pore resulting in downward binding events or resistive pulses.

In one embodiment, the silver nanoneedles of the present invention are fabricated and characterized by electrochemical etching of silver microwire in different conditions. In one embodiment, the present invention forms an AgCl layer around the silver tip prepared in a chloride-containing etchant solution. Measuring the channel current of alpha-hemolysin (αHL) protein pore reconstituted in the lipid bilayer formed at the silver tip was performed, as described in the examples below. The resulting Ag/AgCl nanoneedle-supported biological nanopores mitigate the current decay shown in gold nanoneedles, and thus, allows for more stable, sustained channel current recordings. In another embodiment of the invention, the silver nanoneedle-supported ion channel probe is employed for nanopore sensing of sulfonated β-cyclodextrin (S7βCD).

The feasibility of gold nanoneedles to support a lipid bilayer for ion channel recordings and single-molecule detection has been previously reported. The gold nanoneedle-based ion channel probes have been successfully applied for the chemical detection of sulfonated cyclodextrin (S7βCD) with high spatial resolution. However, in all the previous reports, the gold probes exhibited an open channel current decay as well as a significant decrease in the binding events of S7βCD to αHL pore throughout recording time. The decrease in current is attributed to double layer charging at the gold electrode interface which carries the current at that working electrode. While this decay can be mitigated using asymmetric salt conditions across the lipid bilayer, it is problematic for practical applications of the probe. The present invention uses silver nanoneedle-supported lipid bilayers and biological nanopores in resistive pulse sensing (FIG. 1A). In the examples below, the open channel current resulting from the silver nanoneedle versus the gold nanoneedle was compared. The silver probes of the present invention were fabricated by electrochemical etching of silver microwire to obtain a fine, cone-shaped tip which was then modified with thiol-PEG to support the bilayer formation around the tip. In another embodiment of the present invention, the silver nanoneedle is employed for the single-molecule detection of S7βCD.

In one embodiment, the present invention involves the synthesis of silver nanoneedles by electrochemical etching of silver microwire in perchloric acid solution. These silver nanoneedles are then modified with thiol PEG. Characterization and electrochemical methods were accomplished to understand the surface chemistry of the silver probes before and after modification with thiol PEG. The obtained results suggested the formation of Ag/AgCl surface led to more stable channel current compared to gold. Furthermore, thiol PEG on a silver surface was desorbed with a cathodic peak at −0.85V in 0.1M KOH. As part of the present invention, lipid membrane was successfully formed at the silver tip and the channel current was recorded using αHL protein pore. Finally, these probes were applied for single molecule detection of S7βCD as a target analyte in the concentration range from 1 to 100 μM.)

The present invention enables sustained and stable single channel recordings that can enable the electrochemical imaging and mapping of different surfaces. In addition, the nanoscale geometry of the silver ion channel probe enhances the spatial resolution, rendering highly localized detection measurements more achievable. Further, the present invention allows for the monitoring of cell dynamics by measuring the flux of ions or specific biomolecules.

EXAMPLES

Chemicals and Reagents

A 250 μm diameter silver of 99.99% purity (Alfa Aesar) wire was utilized to fabricate silver nanoneedle. Perchloric acid (70% HClO4; Sigma-Aldrich) and Methanol (HPLC grade; Sigma-Aldrich) were used in a 1:4 solution mixture for electrochemical etching of silver wire. Another etchant solution was prepared from nitric acid (HNO3; Fischer Chemical) and ethanol (ACS-USP grade; Decon labs). O-(3-carboxypropyl)-O'-[2-(3-mercaptopropionylamino)ethyl] propylethylene glycol (MW 3000; Sigma-Aldrich) and O-(2-Carboxyethyl)polyethylene glycol (MW 3,000; Sigma-Aldrich) were used as thiol-PEG and non-thiolated PEG, respectively. Thiol desorption experiments were performed in potassium hydroxide solution (KOH; Fischer Scientific). An electrolyte/buffer solution was made of potassium chloride (KCl; Sigma-Aldrich) or potassium nitrate (KNO3; Sigma-Aldrich) in a sodium phosphate buffer (pH 7.4) composed of sodium dihydrogen phosphate (NaH2PO4·2H2O; Sigma-Aldrich) and disodium phosphate (Na2HPO4). The buffer solution was prepared using ultra-pure water from a Milli-Q (Merck Millipore Corp.) resisted 18.2 MΩ at 25° C. 1,2-Diphytanoyl-sn-glycero-3-phospho-choline (DPhPC; Avanti Polar Lipid) and n-decane (Merck Millipore Corp.) were used as the lipid/oil solution. Alpha-homolysin (αHL; Sigma-Aldrich) isolated from Staphylococcus aureus was purchased as a monomer protein powder. Heptakis(6-O-sulfo)-β-cyclodextrin heptasodium salt (S7βCD; Sigma-Aldrich) was used as the target analyte for single-molecule detection.

Example 1: Fabrication and Characterization of Silver Nanoneedles

A silver nanoneedle was fabricated by electrochemical etching of silver microwire in a methanolic solution of perchloric acid (HClO4:CH3OH, 1:4). The 1-2 mm tip of silver wire was immersed in the etchant solution and a micro-positioner (Newport ULTRAlign 461-XYZ) was used to hold the silver wire vertically. Then, a DC voltage of 1V was applied between the silver microwire and a carbon rod counter electrode (2 mm diameter). The etching process was complete when the current dropped to zero, typically within 4-5 minutes, indicating the silver wire was no longer in contact with the solution. The etched wire with a cone-shaped tip (silver nanoneedle) was then rinsed with deion-ized water (80° C.) and acetone to be characterized. Two Control experiments were performed; etching silver in non-chloride etchant of nitric acid in ethanol solution (HNO3:

C2H5OH; 1:2) and the second control was done by immersion of perchloric acid etched silver in a sodium hypochlorite, solution (8.25%) to chloridate the wire forming Ag/AgCl at the surface. Afterward, the silver tip surface was modified by immersion in a 60 mg/mL thiol-PEG solution in ethanol for 3 h at room temperature and rinsed with ethanol and deionized water. Thiol-PEG provides a support layer for electrolyte solution around the silver tip similar to the previously reported gold nanoneedle. Scanning electron microscopy (Apreo SEM) operated at a voltage of 15 kV was employed to characterize the morphology of the fabricated silver nanoneedles. The surface elemental composition was determined by an X-ray photoelectron spectroscope (XPS) equipped with both Al and Al—Mg dual-core in addition to a helium UV source.

Example 2: Formation of a Lipid Membrane

The lipid bilayer was formed at the silver nanoneedle tip via the tip-dip method. First, a chamber was prepared by adding a buffered 1M KCl electrolyte aqueous phase in the bottom and a lipid/oil mixture (10 mg/mL 1,2-Diphytanoyl-sn-glycero-3-phosphocholine solution in n-decane) at the top. In this arrangement, a lipid monolayer was formed at the interface between the lipid/oil mixture and the electrolyte bath in the chamber. When the PEG-modified silver tip was dipped in the lipid/oil mixture, the aqueous layer around the tip acts as a support for another lipid monolayer formed at the air-water interface with the first withdrawal of the tip from the lipid/oil phase. Then, with the next crossing, the two monolayers were merged to form a lipid bilayer at the silver tip. The movement distance was manipulated by a micro-positioner (Newport ULTRAlign 461-XYZ).

Example 3: Channel Current Recordings of Biological Nanopores

We used αHL protein prepared in 1M KCl/sodium phosphate buffer solution (pH 7.4) at a concentration of 30 nM for channel current recordings. A potential of +100 mV was applied between the silver nanoneedle and a quasi-reference-counter electrode (Ag/AgCl) inserted in the bath chamber. Prior to channel current recordings, the thiol PEG-modified silver nanoneedle was immersed in the electrolyte solution for 10 min to form an aqueous layer around the tip. We used two control silver probes; the first one was dipped in 60 mg/mL non-thiolated PEG instead of thiol-PEG for 3 h, and the second was used without surface modification before immersion in the electrolyte solution. Channel currents were monitored using a patch-clamp amplifier (PICO 2, Tecella) with a 7.9 kHz low-pass filter at a sampling frequency of 40 kHz. Analysis of channel current was performed using pCLAMP version 10.7 (Molecular Devices).

Example 4: Detection of S7βCD and Data Analysis

To employ the fabricated silver probes in resistive pulse nanopore sensing, S7βCD was added as a target analyte in the bath chamber (trans side). We used the thiol-PEG modified silver nanoneedle with αHL protein monomers added in the tip side solution (cis side). In this configuration, the heptameric αHL protein can be reconstituted from the tip side and S7αCD binds to the protein pore from the trans side when a potential of +100 mV was applied. To enhance the capture rate of binding events, we applied an asymmetric salt gradient of 2M/0.5M KCl (trans/cis) and S7βCD was detected at the concentrations of 1 μM, 10 μM, 50 μM, and 100 μM. Channel current data and binding events in an αHL single channel were analyzed using pCLAMP 10.7 and correlated to the concentration of S7βCD.

Example 5: Fabrication and Characterization of Silver Nanoneedles

Figure 2A:
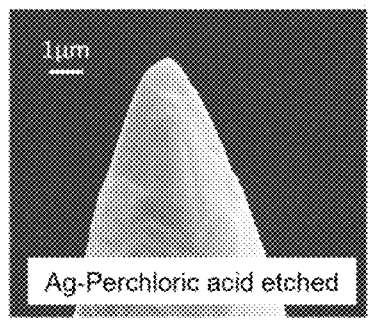
FIG. 2A is a series of SEM micrographs for silver nanoneedle probes prepared by perchloric acid-etching, nitric acid-etching, and bleached silver, respectively from the left to the right.
Figure 2A:
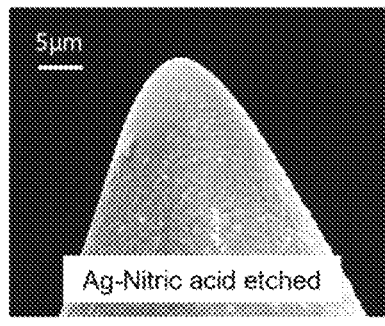
Figure 2A:
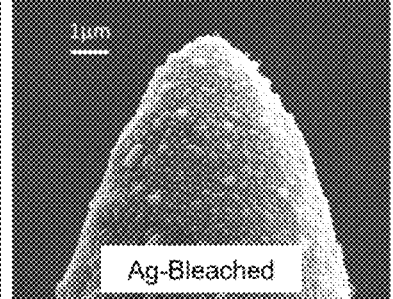

The electrochemical etching protocol for preparing silver tips used in scanning tunneling microscopy was followed to fabricate silver nanoneedles with a cone-shaped tip with an average diameter of 425±33 nm (FIG. 2A). The average tip diameter was measured from high-resolution SEM images for six perchloric acid-etched silver probes. In addition, other silver probes were fabricated in different conditions to be used as a control; the first control was silver etched in the non-chloride etchant solution (2M nitric acid:ethanol, 1:2) and the other control was a bleached silver probe after being etched in perchloric acid solution (FIG. 2A). As a result of varying the electrochemical etching conditions, a variation in the produced tip geometry was observed where the average tip diameter for nitric acid-etched silver nanoneedles was 1.41±0.08 μM, i.e., ~3 folds higher than the perchloric acid-etched probes. The SEM micrograph for the bleached silver probes showed a different surface morphology (FIG. 2A) due to the higher content of AgCl formed on the silver surface. Similar surfaces were shown in previous reports for Ag/AgCl electrodes with high chloride content.

Figure 2B:
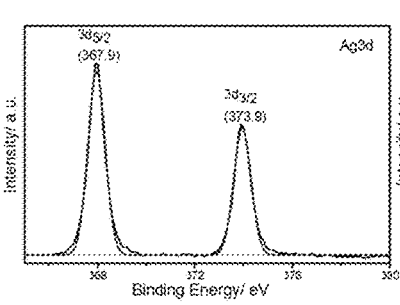
FIG. 2B is the Ag 3d HR-XPS spectra corresponding to the SEM micrographs for the fabricated silver nanoneedles in FIG. 2A.
Figure 2B:
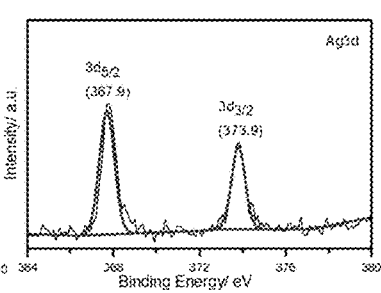
Figure 2B:
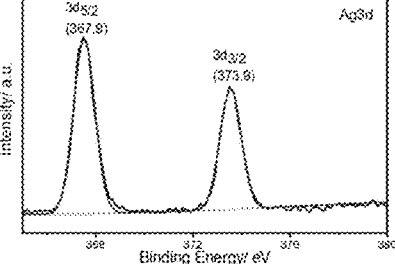
Figure 2C:
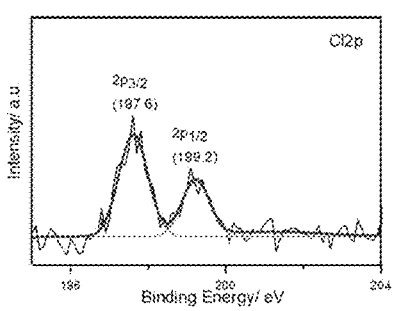
FIG. 2C is the Cl 2p HR-XPS spectra corresponding to the SEM micrographs for the fabricated silver nanoneedles in FIG. 2A.
Figure 2C:
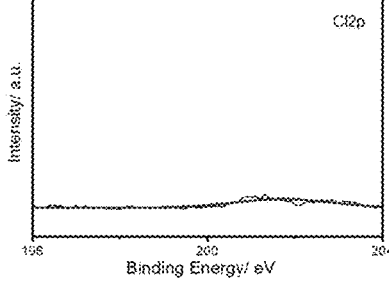
Figure 2C:
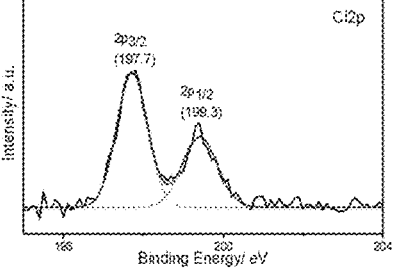

The silver surface is oxidized to silver chloride (AgCl) during the electrochemical etching procedure when performed in a chloride ion-containing solution such as perchloric acid and applying a DC voltage of 1V. To understand the surface chemistry of the fabricated silver probes, we performed X-ray photoelectron spectroscopy (XPS) to elucidate the elemental composition at the silver nanoneedle surface. FIGS. 2B and 2C show the high-resolution XPS spectra of Ag 3d and Cl 2p, respectively, for the three silver nanoneedles prepared in different conditions. The peaks of 3d, inherent to the silver wire, clearly appeared at a binding energy of 367.9 eV and 373.9 eV and were assigned to Ag 3d5/2 and Ag 3d3/2, respectively for all silver probes. However, the Cl 2p peaks were seen only on the perchloric acid-etched probe as well as bleached silver at a binding energy of 197.6 eV and 199.2 eV for 2p3/2 and 2p1/2, respectively. These results indicate that AgCl is formed during the etching of the probe.

Figure 3:
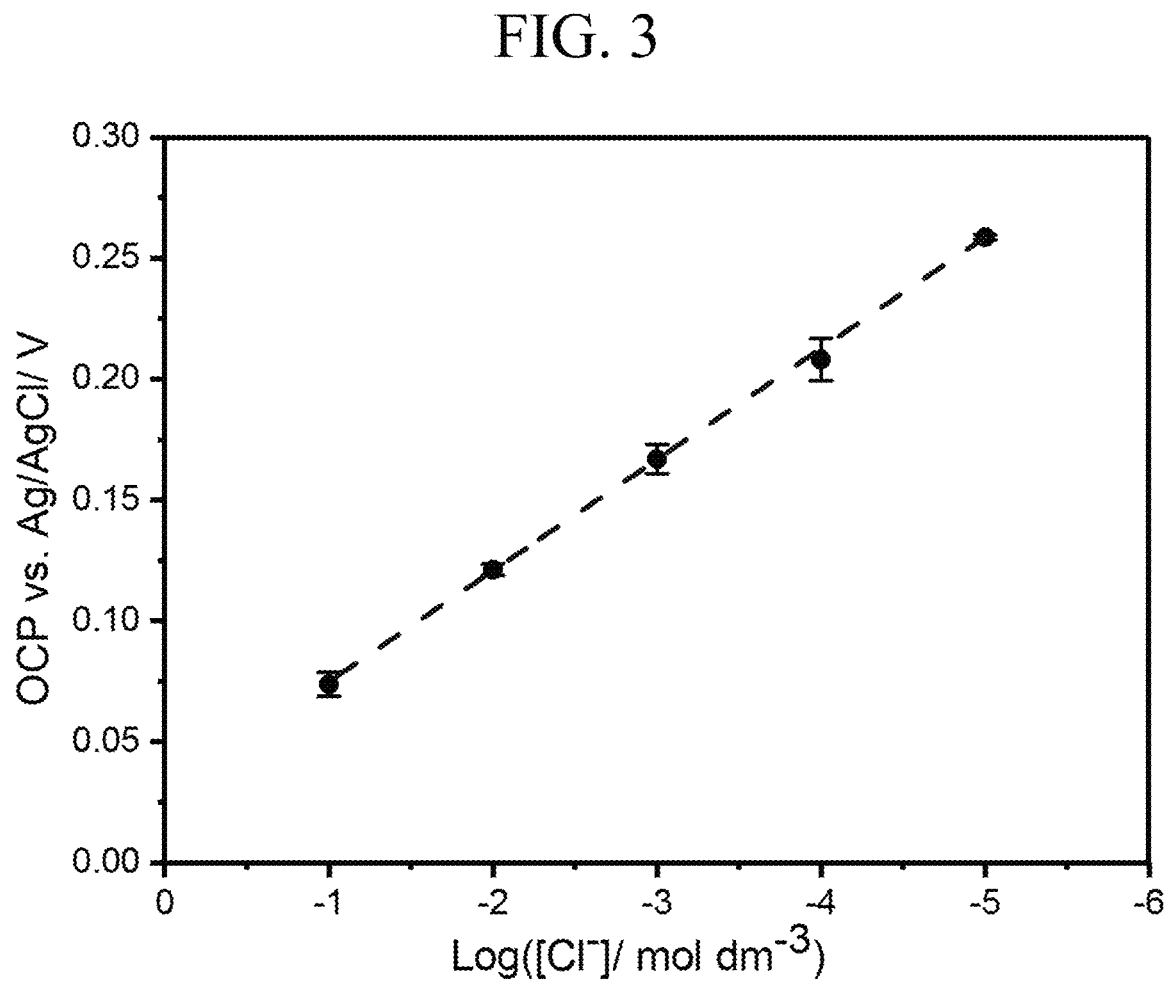

To establish the presence of chloride on the surface of perchloric acid-etched silver, it was demonstrated that these etched silver nanoneedles exhibit Nernstian potential changes to the presence of Cl— in solution. Perchloric acid-etched silver nanoneedles were calibrated in solutions of different chloride activity and the open circuit potential (OCP) was recorded to monitor the potentiometric response in each solution. The probes exhibited Nernstian behavior in a chloride concentration range of 10-5 to 10-1M with a correlation factor (R2) of 0.996 and a gradient of ~50 mV per 10-fold change in chloride ion concentration (FIG. 3). These results are in good agreement with values reported in the literature.

Example 6: Ag Nanoneedle Surface Modification and Formation of a Lipid Membrane To investigate the role of silver nanoneedle surface modification with thiol PEG in supporting protein channel measurement, control experiments were performed using non-thiol PEG (MW 3000) and without PEG for both tip-side insertion and bath-side insertion. The results revealed that the pore conductance and current stability of the αHL protein channels are affected by different surface preparations, especially in the tip-side insertion configuration (in which protein is inserted from the ionic reservoir on the tip side of the lipid bilayer). The silver probes modified with non-thiol PEG or without PEG showed reduced pore conductance and unstable channel current in the tip-side insertion configuration. Contrarily, the nanoneedles modified with thiol PEG exhibited stable current in both tip and bath insertion.

Figure 4:
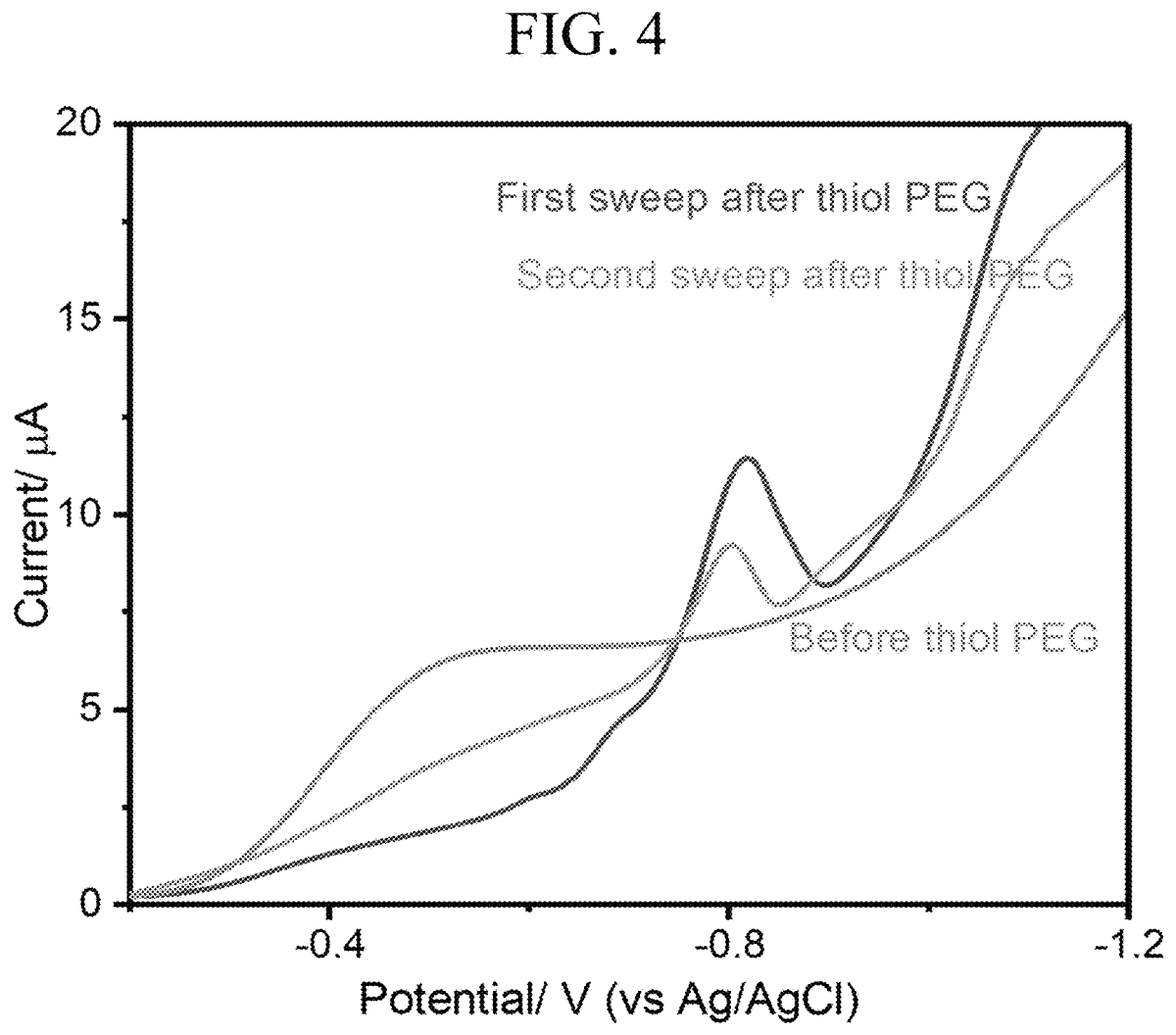

To understand the way that thiol PEG is attached to silver nanoneedle, we used linear sweep voltammetry (LSV) to probe the reductive desorption of Ag-thiol bonds electrochemically. Earlier studies reported the electrochemical desorption of thiolate from Ag electrodes at negative potentials from −0.8V to −1.1V. The reductive desorption experiments were performed in 0.1M KOH (pH=13) for perchloric acid-etched and nitric acid-etched silver nanoneedle. Both perchloric acid-etched and nitric acid-etched silver showed a thiol desorption peak around −0.85V (vs. Ag/AgCl) (FIG. 4). This cathodic peak reduces in intensity with successive sweeps in the same solution as shown in FIG. 4). These findings reveal the reductive desorption of thiolate from the silver nanoneedle indicating that thiol PEG has been chemisorbed on the silver nanoneedle surface.

After surface modification of silver nanoneedle with thiol PEG, an artificial lipid membrane was formed via tip-dip method using the DPhPC/n-decane as a lipid/oil mixture. The thiol PEG layer attached to the silver nanoneedle surface acts as a support for the aqueous solution around the silver tip. In this arrangement, two lipid monolayers are merged; the first monolayer is attached around the probe tip at the air/water interface, where the polar heads of the phospholipids are directed towards the aqueous layer around the tip and the non-polar tails face the air. The second lipid monolayer formed at the interface between the lipid/oil mixture and the electrolyte solution in the bath chamber. The lipid bilayer was successfully formed at the silver nanoneedle tip with a membrane capacitance of 0.42 μF/cm2 in agreement with previously reported lipid membrane capacitance for DPhPC.

Example 7: Channel Current Recordings of Biological Nanopores

Figures 5A, 5B:
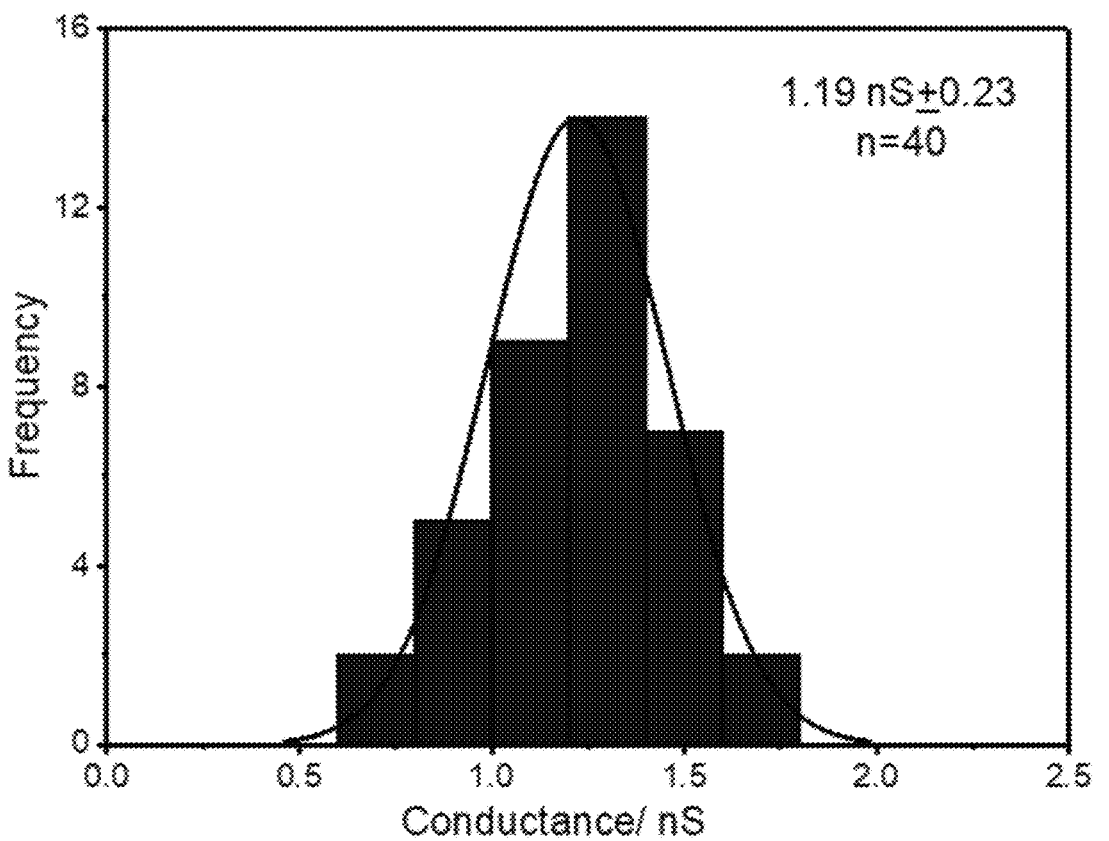
FIG. 5A is an image showing the open channel current for αHL nanopore in 1M KCl solution.
FIG. 5B is a graph showing measured conductance for 40 αHL channels at a potential of 100 mV. The mean pore conductance value was 1.19±0.23 nS.
Figure 6A:
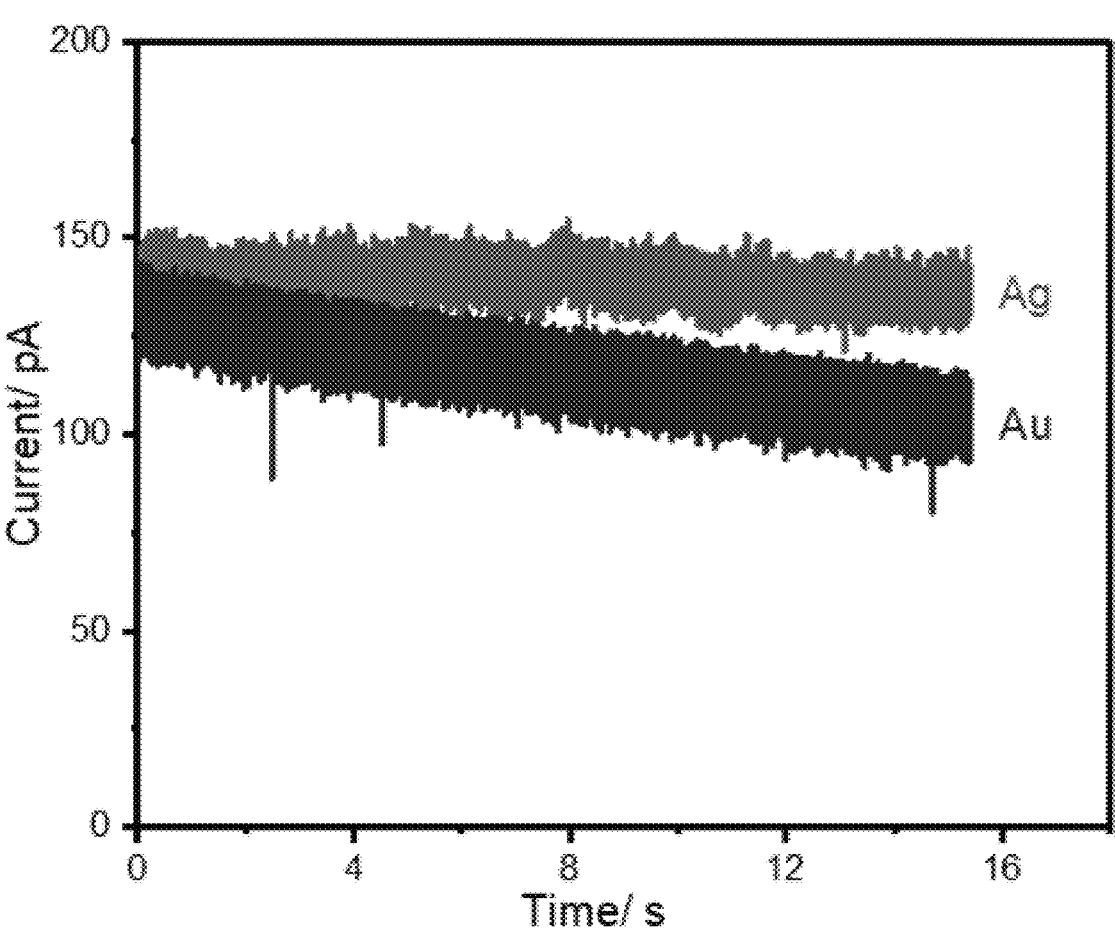
FIG. 6A is a graph showing current-time traces for αHL nanopore using both gold and silver nanoneedles.
Figure 6B:
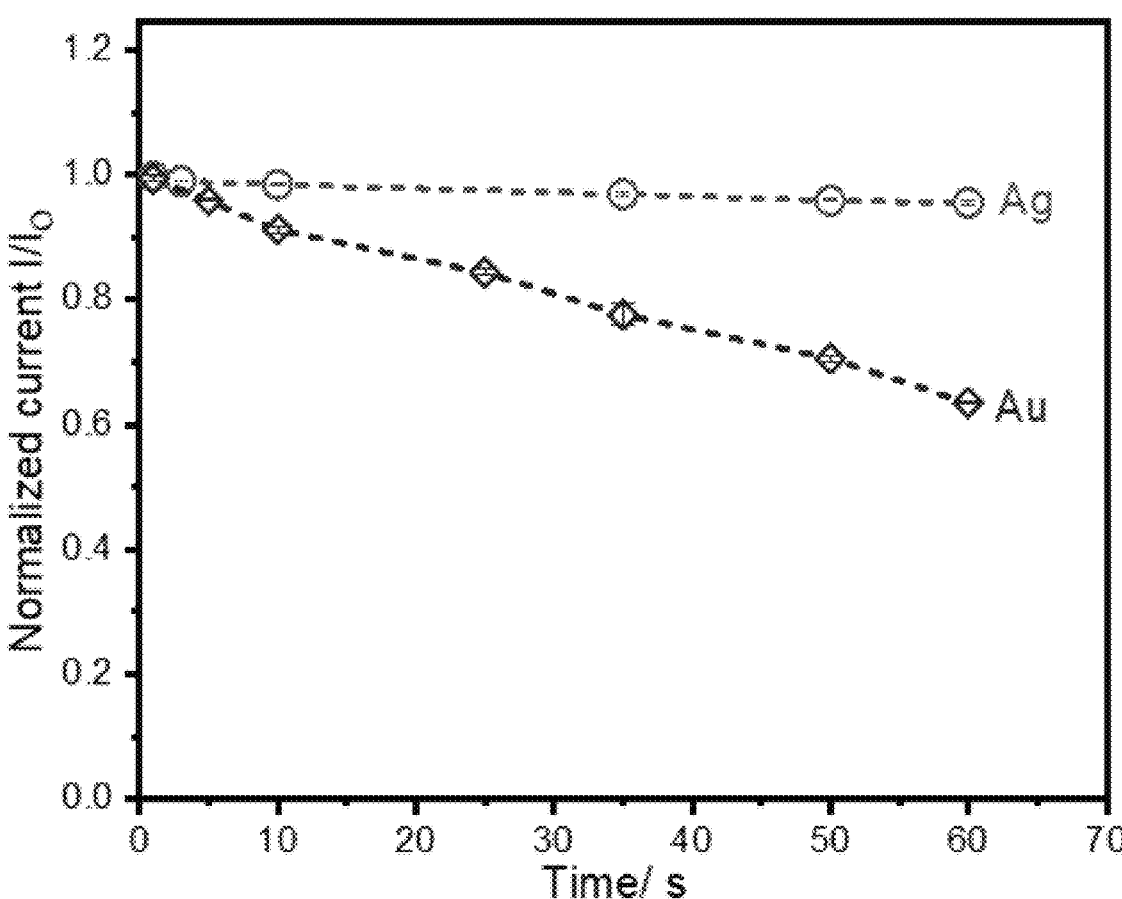
FIG. 6B is a graph showing the average current produced over longer recording time where the channel current showed remarkable decay after 1 minute of recording.
Figure 7:
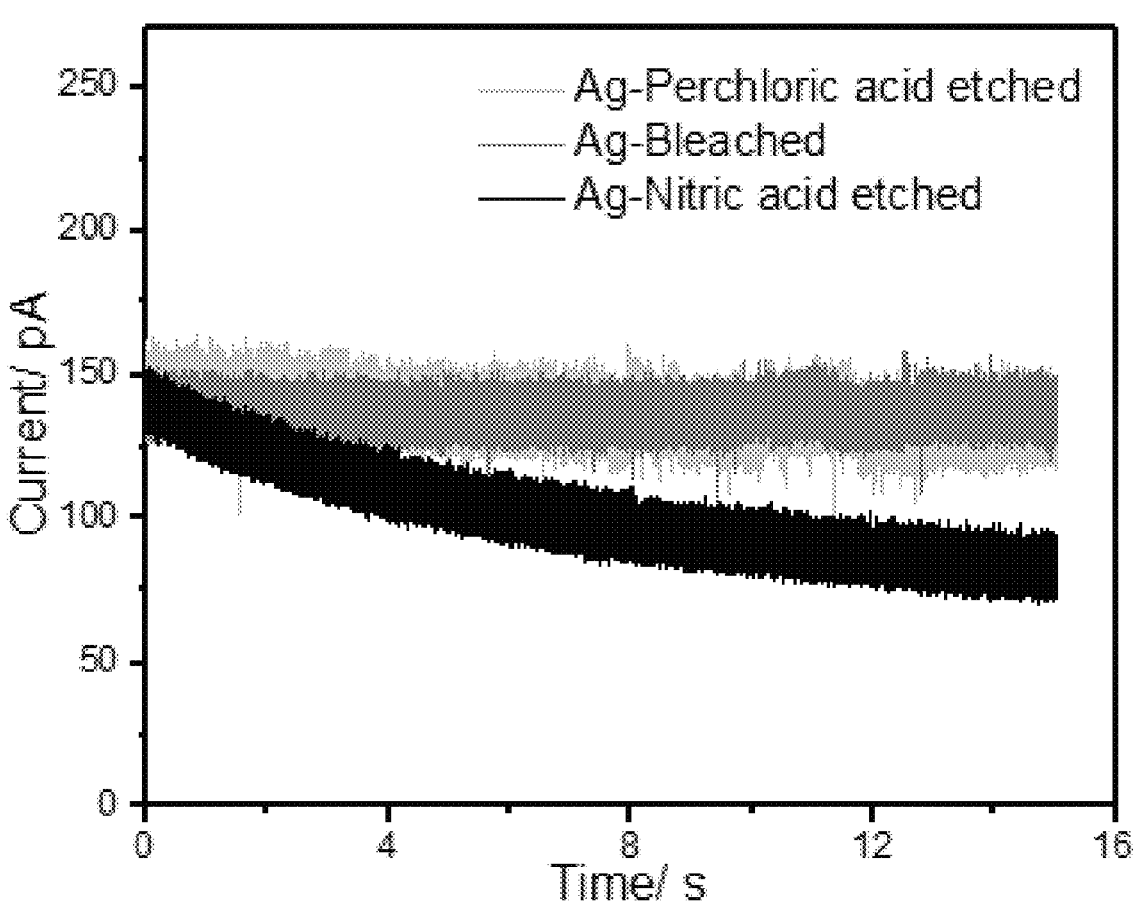
FIG. 7 is a graph showing current-time traces for αHL open channel using silver nanoneedles fabricated with different electrochemical etching conditions. The silver probes prepared in a chloride solution showed more stable current (blue and grey). Etching in a chloride-free solution results in a pristine silver nanoneedle with a current decay over time.

When a stable lipid bilayer was formed, αHL, in a heptameric protein structure, was reconstituted into the lipid membrane. The protein insertion into the lipid bilayer was indicated by a step-like current increase as the transmembrane protein pore allowed for free ion movement between the two electrolyte sides. The αHL pore produced a conductance of 1.19±0.23 nS in 1M KCl symmetric solution conditions (FIG. 5B). In addition, in contrast to the current-time traces on Au nanoneedles, the current-time traces in FIG. 5A indicate a stable open channel current over time. FIGS. 6A and 6B shows a comparison between the current-time traces and the average normalized current for gold and silver nanoneedle-based ion channel probes over the time scale of 15 s and 60 s, respectively. It is clearly seen that the channel current produced from the gold nanoneedle exhibited an exponential decay with time as previously reported by Shoji et al. due to double layer charging at the electrode surface. This current decay was previously explained by Shoji et al. where they stated that the electric double layer capacitance was connected in series with the αHL pore resistance in an equivalent series in the gold nanoneedle set-up. On the other hand, the silver-based ion channel probes resulted in a more stable current over time as shown in FIGS. 5A, 5B, 6A and 6B. Without being bound by theory, it appears that the stable current observed with the silver probe is due to the formation of a layer of AgCl around the silver nanoneedle tip during etching silver electrochemically in perchloric acid. The resulting Ag/AgCl nanoneedle can act as an ideally non-polarizable electrode. More interestingly, we recorded the open channel current for silver nanoneedles prepared in different conditions; the nitric acid-etched and the bleached silver. As demonstrated in FIG. 7, both perchloric acid-etched and bleached silver probes similarly produced a stable current due to the chloride content in the surface. While the silver probe prepared in a chloride-free medium (nitric acid-etched) led to a remarkable current decay (FIG. 7). These results are in agreement with our surface characterization results that revealed the presence of chloride content in the perchloric acid-etched and bleached silver probes while no chloride was found in the nitric acid-etched one (FIGS. 2A-2C and FIG. 3).

Example 8: Detection of S7βCD and Data Analysis

Figure 8A:
FIG. 8A is a series showing single-molecule detection of βCD in a bath side solution. The data shows the frequency of βCD binding events is proportional to the concentration of βCD in the bath solution.
Figure 8A:
Figure 8A:
Figure 8A:
Figure 8B:
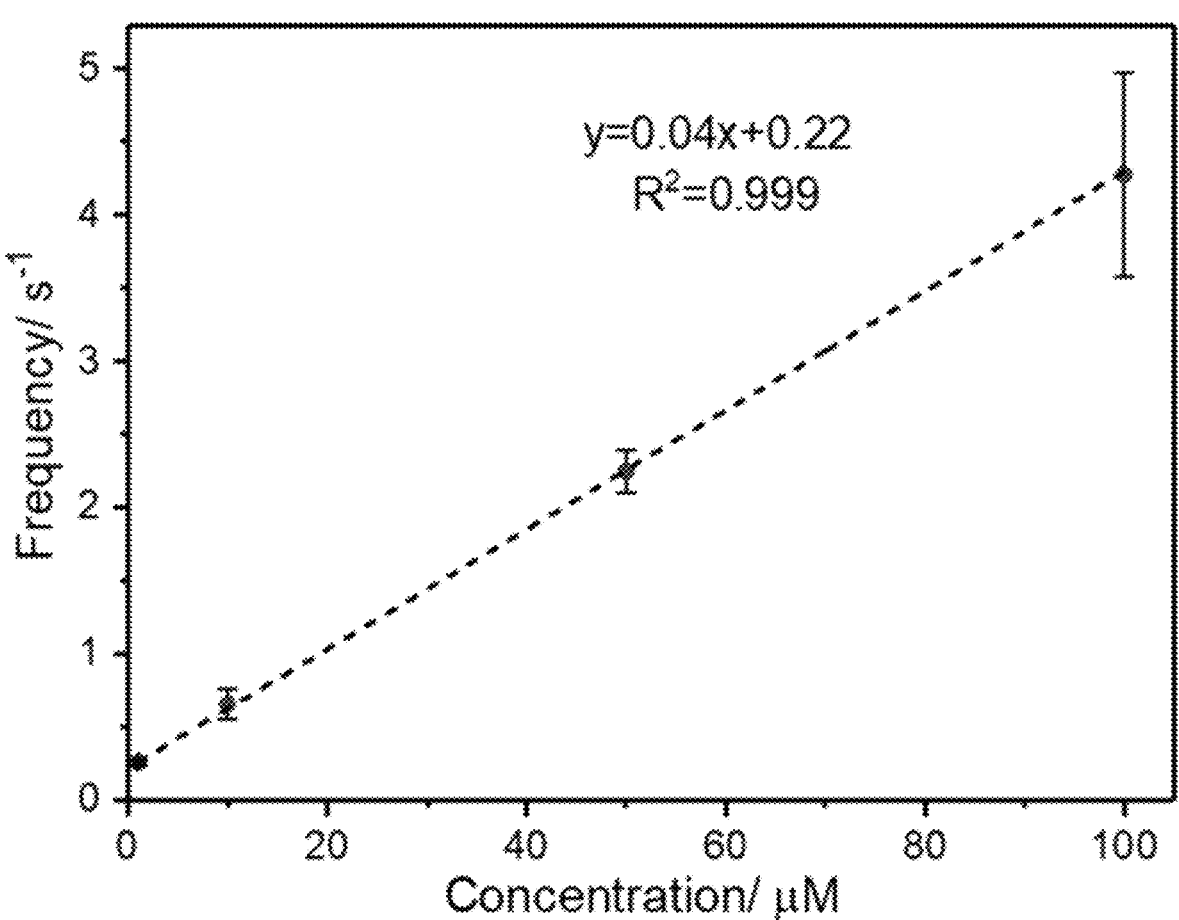
FIG. 8B is a graph showing the calibration curve of βCD. It shows the linear correlation between event frequency and βCD concentration of 1, 10, 50, and 100 μM.
Figure 8C:
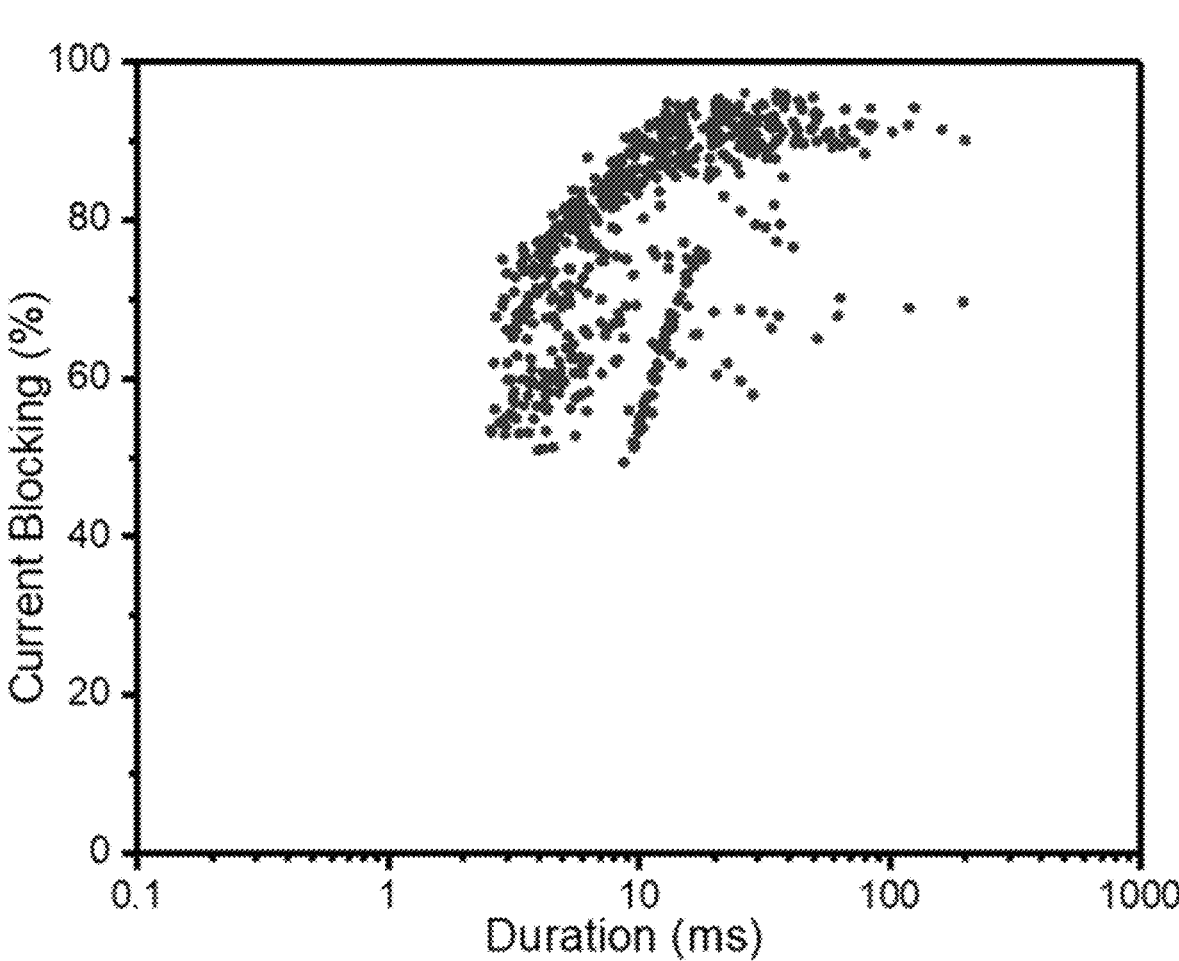
FIG. 8C is a graph showing a scatter plot of the current blockage and dwell time. The median dwell time for blocking events (78% average blockage) was 10 ms.

To employ the silver nanoneedle-based ion channel probe in resistive pulse sensing, the binding events of S7βCD molecules were detected using αHL pore. As S7βCD molecules can access their binding sites in αHL pore from trans side only, S7βCD in bath solution was added and αHL protein solution was present in the tip-side solution at a concentration of 10 nM. To enhance the rate of βCD binding to αHL, an asymmetric salt condition of 2M/0.5M KCl (trans/cis) was used along with applying 1.00 mV. The potential applied across the lipid membrane will produce an electric field around the pore which is the driving force for the particles to arrive at the protein pore. The ion gradient used in asymmetric salt conditions increases the electric field produced resulting in enhancing the capture rate of the target molecule. The binding events of S7βCD were observed and correlated to concentrations of 1, 10, 50, and 100 μM. FIG. 8C shows the number of blocking events due to S7βCD binding to αHL pore increased with higher concentrations. The relationship between binding frequency and S7βCD concentration was linearly fit with a high correlation factor (R2) of 0.999 (n=4) in the concentration range from 1 μM to 100 μM. The dwell time and percent blocking current were also analyzed for 632 binding events of S7βCD where the median current blocking percentage and dwell time of blockage signals were 81.2% and 10 ms, respectively (FIGS. 8A-8C). These results demonstrate the feasibility of the novel silver nanoneedle-based ion channel probe platform as a resistive pulse nanopore sensor.

Example 9

Figure 9:
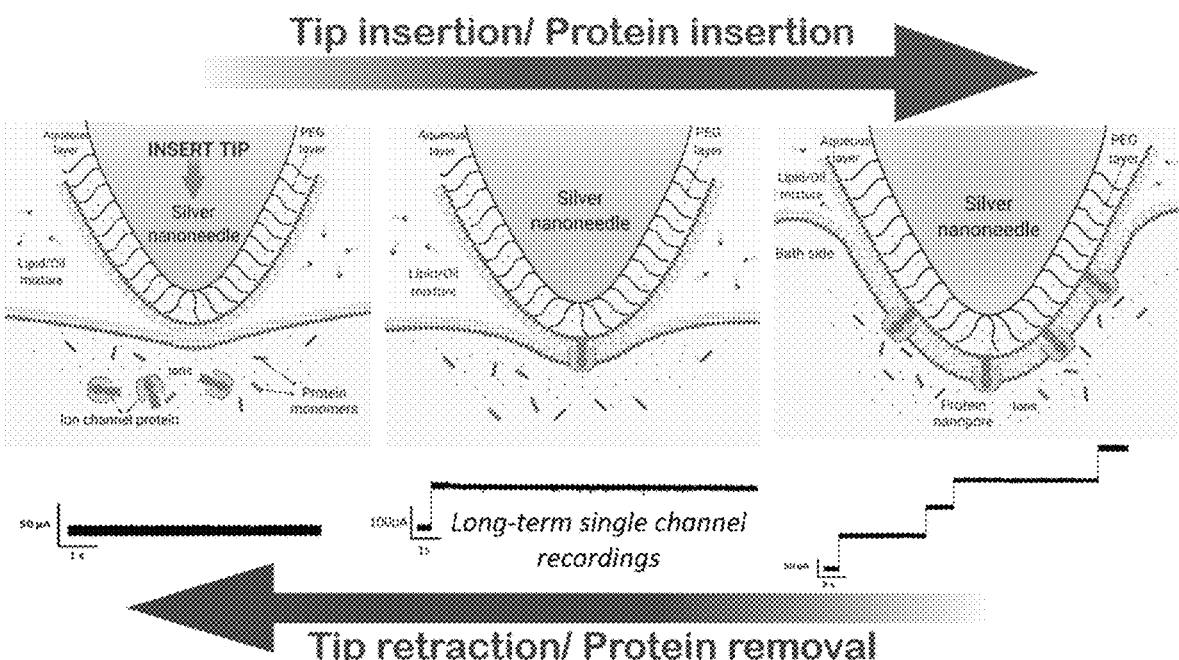
FIG. 9 is a schematic diagram illustrating the mechanism of controlling protein insertion by controlling the vertical movement of silver nanoneedle.
Figure 10:
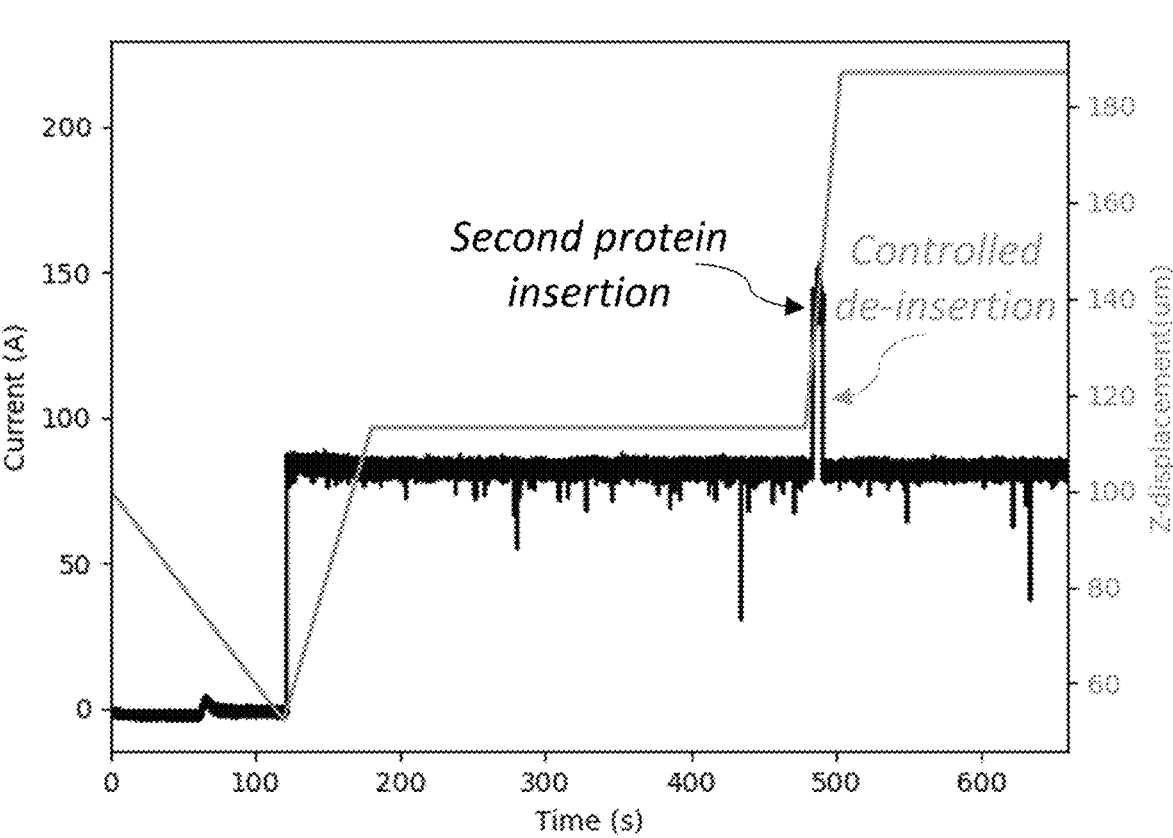
FIG. 10 is a schematic diagram showing the general principle of the current feedback-regulated mechanism to maintain single channel recordings.

In order to maintain long-term single channel recordings (~2 hrs) suitable for future imaging applications, a novel approach was developed, based on the signature channel current events. In this approach, channel current is used as feedback to control the vertical movement of the silver nanoneedle tip so that the number of protein channels inserted in the lipid membrane can be precisely controlled. FIGS. 9 and 10 demonstrate the schematic illustration and the general principle of this approach. FIG. 9 is a schematic diagram illustrating the mechanism of controlling protein insertion by controlling the vertical movement of silver nanoneedle. Left-to-right direction (Blue arrow): moving the silver probe down, or tip insertion, results in multiple protein insertion in the lipid membrane. Right-to-left direction (Pink arrow): moving the silver probe up, or tip retraction, results in proteins de-insertion from the lipid bilayer. This approach is based on controlled vertical movement of the probe to achieve more control over the number of proteins inserted in the lipid membrane and maintain single-channel recordings. FIG. 10 is a schematic diagram showing the general principle of the current feedback-regulated mechanism to maintain single channel recordings. The black graph represents the current-time traces for αHL open channel current, where each current step indicates a single protein insertion. The pink plot illustrates the vertical displacement of the silver probe (right y-axis) with time. The channel current (left y-axis) is used as feedback to control the probe positioning (right y-axis). Once a second protein is inserted (second current step), a "controlled de-insertion" is performed by moving the silver probe up.

Figure 11:
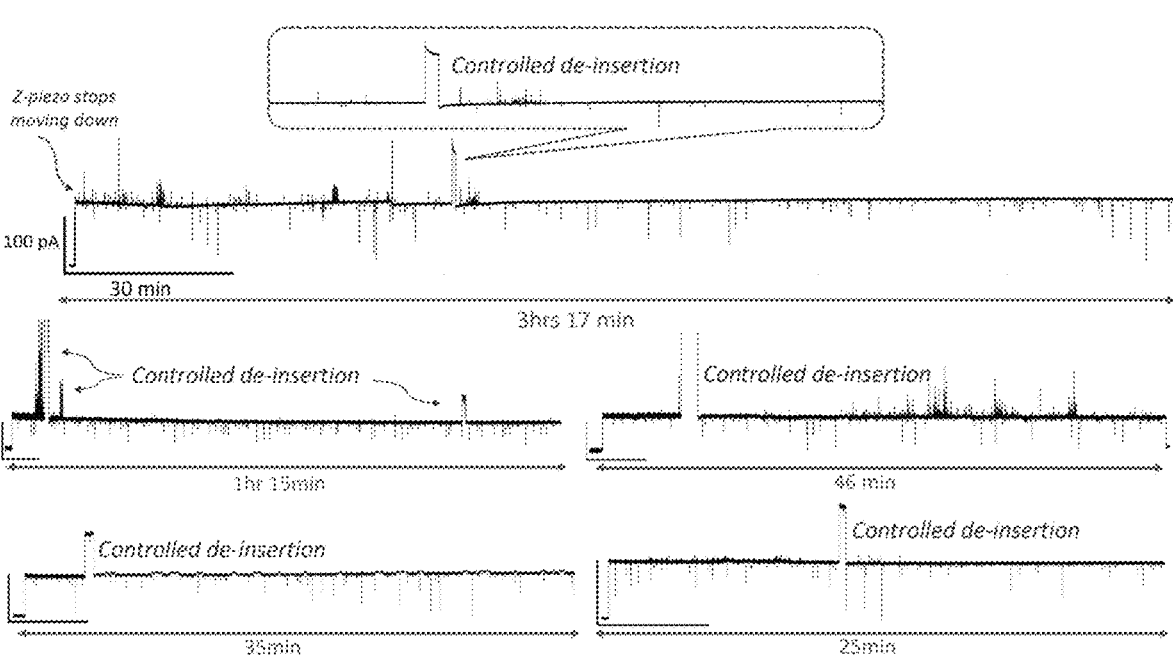
FIG. 11 is a series of long-term measurements for αHL open channel current achieved by using silver nanoneedle ion channel probe and applying the proposed approach of a current feedback-controlled z-displacement of the silver probe.

First, an automated positioning system was used that includes a z-piezo actuator to move the silver probe down across the oil/lipid aqueous interface. This movement enables the bilayer formation as well as protein insertion. However, the z-piezo vertical movement is programmed to stop at a current threshold equivalent to single open channel current value (~100 pA). Therefore, if a second protein is inserted in the bilayer (which will be recognized by a second current step), a "controlled de-insertion" is performed. This is another vertical movement to de-insert the second protein from the lipid membrane. By controlling the z-displacement of the silver tip, a single channel was maintained for a long duration ranging from 25 min to more than 3 hours (FIG. 11). FIG. 11 is a series of long-term measurements for αHL open channel current achieved by using silver nanoneedle ion channel probe and applying the proposed approach of a current feedback-controlled z-displacement of the silver probe. The current-time traces show up to more than 3 hours, stable channel current and performing a controlled de-insertion to remove additional protein insertion. Additionally, further protein insertions could be prohibited, keeping one protein channel over the span of the experiment.

Figure 12:
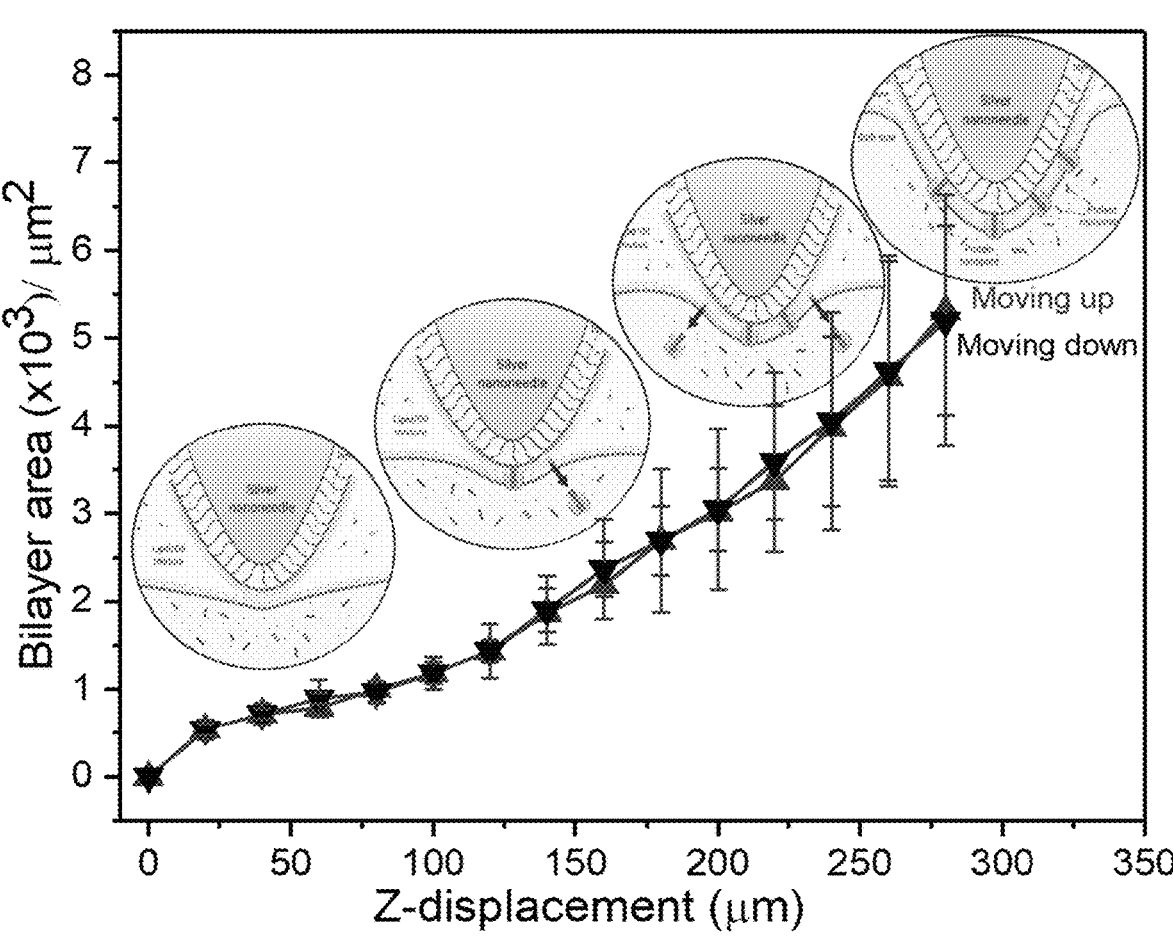
FIG. 12 is a graph showing the correlation between the calculated area of the lipid bilayer and the vertical movement of silver nanoneedle probe.

To quantitively characterize the approach, a correlation between the vertical tip movement and the surface area of the lipid membrane was analyzed. The findings reveal that the area of lipid bilayer decreases with moving of the silver tip up (i.e., decreasing the displacement in the z-direction), as shown in FIG. 12. FIG. 12 is a graph showing the correlation between the calculated area of the lipid bilayer and the vertical movement of silver nanoneedle probe. As illustrated in the inset figures, when moving the probe down (or increasing the Z-displacement), the lipid membrane area increases, resulting in multiple protein insertions. By reducing the Mayer area around the fine silver tip, the probability of multiple insertions and removal of unwanted proteins can be minimized. Thus, long-term single-channel recordings suitable for future applications and mapping different surfaces can be maintained.

Example 10

Figure 13:
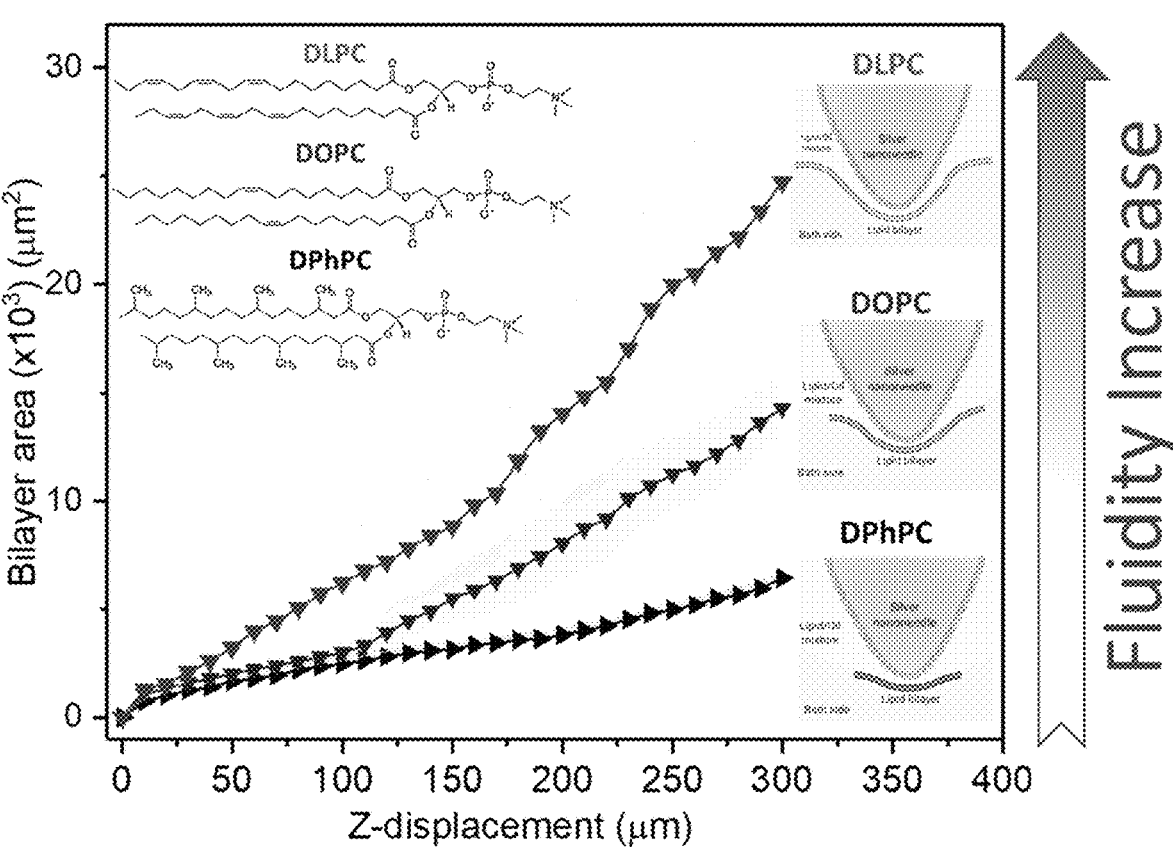
FIG. 13 is a graph showing the change of lipid membrane area vs silver tip displacement for three phospholipids of different fluidity.

The bilayer properties, such as fluidity, were examined to determine how they affect the bilayer shape and area. Bilayer fluidity is a function of different parameters such as fatty acid chain length, fatty acid saturation degree, temperature, and charge. The bilayer fluidity was adjusted by varying the unsaturation degree of the hydrocarbon fatty acid tails in the phospholipids. The arrangement of the fatty acid hydrocarbon interior of the lipid bilayer plays a key role in the formed bilayer area. Saturated fatty acid tails with linear arrangement of hydrocarbons, such as DPhPC, results in tight packing of lipid molecules. While the kinks in the double bonds of the unsaturated fatty acids disorder the packing of the hydrocarbon chain, leading to more fluid structures. Three different phospholipids were used: saturated phospholipid (DPhPC), unsaturated with two double bonds (DOPC), and unsaturated with six double bonds (DLPC). FIG. 13 shows the correlation between the bilayer area formed using the different phospholipids and Z-positions of the silver tip. The higher degree of fatty acid unsaturation, the higher bilayer fluidity, and the larger lateral surface area. The kinked tails of unsaturated fatty acid occupy a larger lateral surface area when packed within the bilayers compared to a straight lipid tail of saturated fatty acids. FIG. 13 is a graph showing the change of lipid membrane area vs silver tip displacement for three phospholipids of different fluidity. More fluid lipids resulted in larger surface area for the lipid bilayer formed around the silver nanoneedle tip. Fluidity increases as the degree of unsaturation of phospholipids increases as shown in the chemical structures (top left corner).

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A composition comprising one or more nanoneedles, wherein each nanoneedle has a silver tip and one or more of the silver tips comprise a layer of silver chloride (AgCl); and further, wherein the nanoneedles are silver microwire electrochemically etched with a perchloric acid solution.

2. The composition of claim 1 wherein one or more of the silver tips further comprise a layer comprising thiol-polyethylene glycol.

3. The composition of claim 1 wherein one or more of the silver tips are conical in shape.

4. The composition of claim 1 wherein the one or more nanoneedles have an average diameter from about 300 nm to about 600 nm.

5. The composition of claim 1 wherein the one or more nanoneedles have an average diameter from about 425 nm.

6. A method of resistive pulse detection involving a protein pore comprising:
   a. reconstituting one or more protein pores in a lipid membrane formed on the tip of a nanoneedle, wherein the nanoneedle has a silver tip and one or more of the silver tips comprise an AgCl layer;
   b. applying a potential across the membrane;
   c. detecting resistive pulses;
   wherein the nanoneedle is a silver microwire electrochemically etched with a perchloric acid solution.

7. The method of claim 6 wherein one or more of the silver tips further comprise a layer comprising thiol-polyethylene glycol.

8. The method of claim 6 wherein one or more of the silver tips are conical in shape.

9. The method of claim 6 wherein the one or more nanoneedles have an average diameter from about 300 nm to about 600 nm.

10. The method of claim 6 wherein the one or more nanoneedles have an average diameter from about 425 nm.

11. The method of claim 6 further comprising using data including the resistive pulses to identify a type of molecule.

12. The method of claim 11 wherein the data comprises the magnitude, duration, and frequency of transient blockages.

\* \* \* \* \*